United States Patent [19]

Hofer et al.

[11] 4,163,052
[45] Jul. 31, 1979

[54] PESTICIDAL O-[3-T-BUTYLPYRAZOL-5-YL]PHOSPHORIC AND THIONOPHOSPHORIC ACID ESTERS

[75] Inventors: Wolfgang Hofer; Fritz Maurer; Hans-Jochem Riebel; Rolf Schröder, all of Wuppertal; Wolfgang Behrenz, Overath; Ingeborg Hammann, Cologne; Bernhard Homeyer, Leverkusen, all of Fed. Rep. of Germany

[73] Assignee: Bayer Aktiengesellschaft, Leverkusen, Fed. Rep. of Germany

[21] Appl. No.: 827,512

[22] Filed: Aug. 24, 1977

[30] Foreign Application Priority Data

Sep. 1, 1976 [DE] Fed. Rep. of Germany ....... 2639258

[51] Int. Cl.² .......................... A01N 9/36; C07F 9/65
[52] U.S. Cl. .................... 424/200; 548/375; 548/376; 548/377
[58] Field of Search ..................... 548/375, 376, 377; 424/200

[56] References Cited

U.S. PATENT DOCUMENTS

| 3,010,969 | 11/1961 | Rigterink | 548/375 |
| 3,216,894 | 11/1965 | Lorenz et al. | 548/375 |
| 3,825,557 | 7/1974 | Hoffmann et al. | 424/200 |

FOREIGN PATENT DOCUMENTS 713278  8/1954  United Kingdom ..................... 548/375

Primary Examiner—John M. Ford
Assistant Examiner—Natalia Harkaway
Attorney, Agent, or Firm—Sprung, Felfe, Horn, Lynch & Kramer

[57] ABSTRACT

O-[3-tert.-butyl-pyrazol(5)yl]-(thiono)(thiol)-phosphoric(phosphonic) acid esters and ester amides of the formula

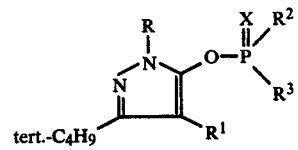

in which
R is hydrogen, alkyl, cyanoalkyl, or phenyl optionally carrying at least one halogen, halogenoalkyl, alkyl or alkylthio substituent,
$R^1$ is hydrogen, halogen, alkyl or alkylthio,
$R^2$ is alkoxy, alkyl or phenyl,
$R^3$ is alkoxy, alkylthio or monoalkylamino, and
X is oxygen or sulphur, which possess arthropodicidal, nematicidal and fungicidal properties.

10 Claims, No Drawings

PESTICIDAL O-[3-T-BUTYLPYRAZOL-5-YL]PHOSPHORIC AND THIONOPHOSPHORIC ACID ESTERS

The present invention relates to and has for its objects the provision of particular new O-[3-tert.-butyl-pyrazol(5)yl]-(thiono)(thiol)-phosphoric(phosphonic) acid esters and ester-amides which possess arthropodicidal, nematicidal and fungicidal properties, active compositions in the form of mixtures of such compounds with solid and liquid dispersible carrier vehicles, and methods for producing such compounds and for using such compounds in a new way especially for combating pests with other and further objects becoming apparent from a study of the within specification and accompanying examples.

It is known from U.S. Pat. No. 2,754,244 that certain methyl-substituted pyrazolyl-thiono-phosphoric acid esters, for example O,O-diethyl-O-[3-dimethylpyrazol(-5)yl]-thionophosphoric acid ester (Compound A), possess insecticidal and acaricidal properties.

The present invention now provides, as new compounds, the tert.-butyl-substituted pyrazolyl(thiono)(thiol)-phosphoric(phosphonic) acid esters and ester-amides of the general formula

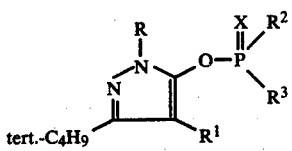

in which

R represents hydrogen, alkyl, cyanoalkyl or phenyl, the phenyl ring optionally carrying one or more substituents selected independently from halogen, or halogenoalkyl, alkyl and alkylthio with up to 4 carbon atoms, $R^1$ represents hydrogen, halogen, or alkyl or alkylthio with up to 6 carbon atoms, $R^2$ represents alkoxy, alkyl or phenyl, $R^3$ represents alkoxy, alkylthio or monoalkylamino, and X represents oxygen or sulphur.

Preferably, R represents hydrogen, straight-chain or branched alkyl or cyanoalkyl, each with 1 to 4 (especially 1 or 2) alkyl carbon atoms, or phenyl, optionally carrying from one to five substituents selected independently from chlorine, methyl, ethyl and trifluoromethyl, $R^1$ represents hydrogen, chlorine, bromine or straight-chain or branched alkyl with 1 to 6 (especially 1 to 4) carbon atoms, $R^2$ represents straight-chain or branched alkoxy or alkyl, each with 1 to 8 (especially with 1 to 5) carbon atoms, or phenyl, $R^3$ represents straight-chain or branched alkoxy, alkylthio or monoalkylamino, each with 1 to 6 (especially with 1 to 4) carbon atoms, and X represents sulphur.

Surprisingly, the tert.-butyl-substituted pyrazolyl(thiono)(thiol)-phosphoric(phosphonic) acid esters and ester-amides according to the invention exhibit a better insecticidal, acaricidal and nematicidal action than the previously known methyl-substituted pyrazolylthionophosphoric acid esters of analogous structure and of the same type of action. The compounds according to the invention thus represent a genuine enrichment of the art.

The invention also provides a process for the preparation of a tert.-butyl-substituted pyrazolyl(thiono)(thiol)-phosphoric(phosphonic) acid ester or ester amide of the formula (I) in which a (thiono)(thiol)-phosphoric(phosphonic) acid ester halide or ester-amide halide of the general formula

in which $R^2$, $R^3$ and X have the abovementioned meanings and Hal represents halogen, preferably chlorine, is reacted, if appropriate in the presence of a diluent or solvent, with a 3-tert.-butyl-5-hydroxy-pyrazole of the general formula

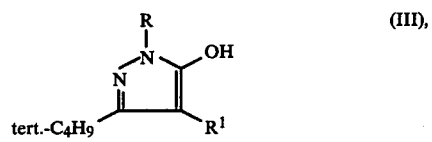

in which

R and $R^1$ have the abovementioned meanings, the latter being reacted as such, in the presence of an acid acceptor, or in the form of an alkali metal salt, alkaline earth metal salt or ammonium salt.

If, for example, O-n-propylthionophenylphosphonic acid ester chloride and 1,4-diethyl-3-tert.-butyl-5-hydroxy-pyrazole are used as starting materials, the course of the reaction can be represented by the following equation:

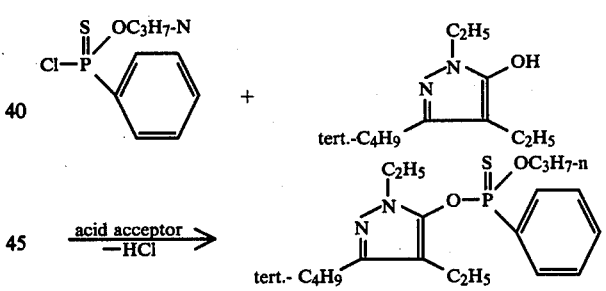

The (thiono)(thiol)-phosphoric(phosphonic) acid ester halides and ester-amide halides (II) to be used as starting materials are known and can readily be prepared, even industrially, in accordance with processes known from the literature. The following may be mentioned as individual examples: O,O-dimethyl-, O,O-diethyl-, O,O-di-n-propyl-, O,O-di-isopropyl, O,O-di-n-butyl-, O,O-di-iso-butyl, O,O-di-sec.-butyl-, O-methyl-O-ethyl-, O-methyl-O-n-propyl-, O-methyl-O-iso-propyl-, O-methyl-O-n-butyl-, O-methyl-O-iso-butyl-, O-methyl-O-sec.-butyl-, O-ethyl-O-n-propyl, O-ethyl-O-iso-propyl-, O-ethyl-O-n-butyl, O-ethyl-O-sec.-butyl-, O-ethyl-O-iso-butyl-, O-n-propyl-O-butyl, O-iso-propyl-O-n-butyl-, O-ethyl-O-n-pentyl- and O-n-propyl-O-n-pentyl-thionophosphoric acid diester chloride; O,S-dimethyl-, O,S-diethyl-, O,S-di-n-propyl-, O,S-di-iso-propyl-, O,S-di-n-butyl, O,S-di-iso-butyl-, O,S-di-n-pentyl-, O-ethyl-S-n-propyl-, O-ethyl-S-iso-propyl-, O-ethyl-S-n-butyl-, O-ethyl-S-sec.-butyl-, O-n-propyl-S-ethyl-, O-n-propyl-S-iso-propyl-, O-n-butyl-S-n-propyland O-sec.-butyl-S-ethyl-thionothiolphosphoric acid diester chloride; O-methyl-, O-ethyl-, O-n-propyl-, O-iso-propyl-, O-n-butyl-, O-iso-butyl-, O-sec.-butyl- and O-n-pentyl-methane-, -ethane-, -n-propane-, -iso-propane-, -n-butane-, -iso-butane-, -sec.-butane-, -n-pentane- and -phenyl-thionophosphonic acid ester chloride; S-methyl-, S-ethyl-, S-n-propyl-, S-iso-propyl-, S-n-butyl-, S-iso-butyl-, S-sec.-butyl- and S-n-pentyl-methane-, -ethane-, -n-propane-, -iso-propane-, -n-butane-, -iso-butane-, -sec.-butane- and -phenyl-thionothiolphosphonic acid ester chloride; O-methyl-N-methyl-, O-methyl-N-ethyl-, O-methyl-N-n-propyl-, O-methyl-N-iso-propyl-, O-ethyl-N-methyl-, O-ethyl-N-ethyl-, O-ethyl-N-n-propyl-, O-ethyl-N-iso-propyl-, O-n-propyl-N-methyl-, O-n-propyl-N-ethyl-, O-n-propyl-N-n-propyl-, O-n-propyl-N-iso-propyl-, O-iso-propyl-N-methyl-, O-iso-propyl-N-ethyl-, O-iso-propyl-N-n-propyl-, O-iso-propyl-N-iso-propyl-, O-n-butyl-N-methyl-, O-n-butyl-N-ethyl-, O-n-butyl-N-n-propyl-, O-n-butyl-N-iso-propyl-, O-iso-butyl-N-methyl-, O-iso-butyl-N-ethyl-, O-iso-butyl-N-n-propyl-, O-iso-butyl-N-iso-propyl-, O-sec.-butyl-N-methyl-, O-sec.-butyl-N-ethyl-, O-sec.-butyl-N-n-propyl-, O-sec.-butyl-N-iso-propyl-, O-methyl-N-n-butyl-, O-ethyl-N-n-butyl-, O-n-propyl-N-n-butyl-, O-ethyl-N-sec.-butyl-, O-n-propyl-N-sec.-butyl- and O-iso-propyl-N-sec.-butyl-thionophosphoric acid ester-amide chloride.

The 3-tert.-butyl-5-hydroxy-pyrazoles (III), which are also to be used as starting materials, can be prepared in accordance with processes known from the literature, by reacting pivaloylacetic acid alkyl ester derivatives with hydrazine derivatives, if appropriate in the presence of an alcoholate, in accordance with the following equation:

$$RNH-NH_2 + tert.-C_4H_9-CO-CHR^1-CO-OAlkyl$$

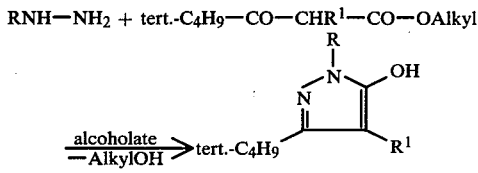

The following may be mentioned as individual examples of such compounds: 3-tert.-butyl-5-hydroxy-pyrazole, as well as 1-methyl-, 1-ethyl-, 1-(2-cyanoethyl)-, 1-phenyl-, 1-(3-chlorophenyl)-, 1-(4-chlorophenyl)-, 1-(3-bromophenyl)-, 1-(4-bromophenyl)-, 1-(4,6-dichlorophenyl)-, 1-(4,6-dibromophenyl)-, 1-(4-methylphenyl)-, 1-(4-ethylphenyl)-, 1-(3-trifluoromethylphenyl)-, 1-methyl-4-chloro-, 1-ethyl-4-chloro-, 1-(2-cyanoethyl)-4-chloro-, 1-phenyl-4-chloro-, 1-(3-chloro-phenyl)-4-chloro, 1-(4-chlorophenyl)-4-chloro-, 1-(3-bromo-phenyl)-4-chloro-, 1-(4-bromophenyl)-4-chloro-, 1-(4,6-dichlorophenyl)-4-chloro-, 1-(4,6-dibromophenyl)-4-chloro-, 1-(4-methylphenyl)-4-chloro-, 1-(4-ethylphenyl)-4-chloro-, 1-(3-trifluoromethylphenyl)-4-chloro-, 1-methyl-4-bromo-, 1-ethyl-4-bromo-, 1-(2-cyanoethyl)-4-bromo-, 1-phenyl-4-bromo-, 1-(3-chlorophenyl)-4-bromo-, 1-(3-bromophenyl)-4-bromo-, 1-(4-bromophenyl)-4-bromo-, 1-(4,6-dichloro-phenyl)-4-bromo-, 1-(4,6-dibromophenyl)-4-bromo-, 1-(4-methylphenyl)-4-bromo-, 1-(4-ethylphenyl)-4-bromo-, 1-(3-trifluoromethylphenyl)-4-bromo-, 1,4-dimethyl-, 1-ethyl-4-methyl-, 1-(2-cyanoethyl)-4-methyl-, 1-phenyl-4-methyl-, 1-(3-chlorophenyl)-4-methyl-, 1-(4-chlorophenyl)-4-methyl-, 1-(3-bromophenyl)-4-methyl-, 1-(4-bromophenyl)-4-methyl-, 1-(4,6-dichlorophenyl)-4-methyl-, 1-(4,6-dibromophenyl)-4-methyl-, 1-(4-methylphenyl)-4-methyl-, 1-(4-ethylphenyl)-4-methyl-, 1-(3-trifluoromethylphenyl)-4-methyl-, 1-methyl-4-ethyl-, 1,4-diethyl-, 1-(2-cyanoethyl)-4-ethyl-, 1-phenyl-4-ethyl-, 1-(3-chlorophenyl)-4-ethyl-, 1-(4-chlorophenyl)-4-ethyl-, 1-(3-bromophenyl)-4-ethyl-, 1-4-bromophenyl)-4-ethyl-, 1-(4,6-dichlorophenyl)-4-ethyl-, 1-(4,6-dibromophenyl)-4-ethyl-, 1-(4-methylphenyl)-4-ethyl-, 1-(4-ethylphenyl)-4-ethyl-, 1-(3-trifluoromethylphenyl)-4-ethyl-, 1-methyl-4-n-propyl-, 1-ethyl-4-n-propyl-, 1-(2-cyanoethyl)-4-n-propyl-, 1-phenyl-4-n-propyl-, 1-(3-chlorophenyl)-4-n-propyl-, 1-(4-chlorophenyl)-4-n-propyl-, 1-(3-bromophenyl)-4-n-propyl-, 1-(4-bromophenyl)-4-n-propyl-, 1-(4,6-dichlorophenyl)-4-n-propyl-, 1-(4,6-dibromophenyl)-4-n-propyl-, 1-(4-methylphenyl)-4-n-propyl-, 1-(4-ethylphenyl)-4-n-propyl-, 1-(3-trifluoromethylphenyl)-4-n-propyl-, 1-methyl-4-iso-propyl-, 1-ethyl-4-iso-propyl-, 1-(2-cyanoethyl)-4-iso-propyl-, 1-phenyl-4-iso-propyl-, 1-(3-chlorophenyl)-4-iso-propyl-, 1-(4-chlorophenyl)-4-iso-propyl-, 1-(3-bromophenyl)-4-iso-propyl-, 1-(4-bromophenyl)-4-iso-propyl-, 1-(4,6-dichlorophenyl)-4-iso-propyl-, 1-(4,6-dibromophenyl)-4-iso-propyl-, 1-(4-methylphenyl)-4-iso-propyl-, 1-(4-ethylphenyl)-4-iso-propyl-, 1-(3-trifluoromethylphenyl)-4-iso-propyl-, 1-methyl-4-n-butyl-, 1-ethyl-4-n-butyl-, 1-(2-cyanoethyl)-4-n-butyl-, 1-phenyl-4-n-butyl-, 1-(3-chlorophenyl)-4-n-butyl-, 1-(4-chlorophenyl)-4-n-butyl-, 1-(3-bromophenyl)-4-n-butyl-, 1-(4-bromophenyl)-4-n-butyl-, 1-(4,6-dichlorophenyl)-4-n-butyl-, 1-(4,6-dibromophenyl)-4-n-butyl-, 1-(4-methylphenyl)-4-n-butyl-, 1-(4-ethylphenyl)-4-n-butyl- and 1-(3-trifluoromethylphenyl)-4-n-butyl-3-tert.-butyl-5-hydroxy-pyrazole.

The process for the preparation of the compounds according to the invention is preferably carried out in the presence of a suitable solvent or diluent. Virtually all inert organic solvents can be used for this purpose, especially aliphatic and aromatic, optionally chlorinated, hydrocarbons, such as benzene, toluene, xylene, benzine, methylene chloride, chloroform, carbon tetrachloride and chlorobenzene; esters, for example diethyl ether, dibutyl ether and dioxane; ketones, for example acetone, methyl ethyl ketone, methyl isopropyl ketone and methyl isobutyl ketone; and nitriles, such as acetonitrile and propionitrile.

All customary acid-binding agents can be used as acid acceptors. Alkali metal carbonates and alkali metal alcoholates, such as sodium carbonate and potassium carbonate, sodium methylate and ethylate and potassium methylate and ethylate, have proved particularly suitable, as have aliphatic, aromatic or heterocyclic amines, for example triethylamine, trimethylamine, dimethylaniline, dimethylbenzylamine and pyridine.

The reaction temperature can be varied within a fairly wide range. In general, the reaction is carried out at from 0° to 120° C., preferably at from 10° to 60° C.

The reaction is in general allowed to take place under normal pressure.

To carry out the process, the starting materials are in most cases employed in equimolar amounts. An excess of one or other component produces no essential advantages. The reactants are brought together, in most cases in one of the abovementioned solvents, and are stirred for one or more hours at an elevated temperature to complete the reaction. After cooling the mixture, an organic solvent, for example toluene, is added thereto, and the organic phase is worked up in the usual manner by washing, drying and distilling off the solvent.

The new compounds are obtained in the form of oils, which in most cases cannot be distilled without decomposition, but are freed from the last volatile constituents by so-called "slight distillation", that is to say by prolonged heating under reduced pressure to moderately elevated temperatures, and are purified in this manner. They are characterized by the refractive index.

As already mentioned, the tert.-butyl-substituted pyrazolyl(thiono)(thiol)-phosphoric(phosphonic) acid esters and ester-amides according to the invention are distinguished by an excellent insecticidal, acaricidal and nematicidal activity. Some compounds also exhibit fungicidal properties. They are not only active against plant pests, pests harmful to health and pests of stored products, but also, in the veterinary medicine field, against animal parasites (ecto-parasites). They combine a low phytotoxicity with a good action against both sucking and biting insects and mites.

For this reason, the compounds according to the invention can be employed successfully as pesticides in plant protection as well as in the hygiene field, the field of protection of stored products and the veterinary field.

The active compounds are well tolerated by plants, have a favorable level of toxicity to warm-blooded animals, and can be used for combating arthropod pests, especially insects and arachnids, and nematode pests which are encountered in agriculture, in forestry, in the protection of stored products and of materials, and in the hygiene field. They are active against normally sensitive and resistant species and against all or some stages of development. The abovementioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and Scutigera spec.; from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria;* from the order of the Dermaptera, for example *Forficula auricularia;* from the order of the Isoptera, for example Reticulitermes spp.; from the order of the Anoplura, for example *Phylloxera vastatrix,* Pemphigus spp.; *Pediculus humanus corporis,* Haematopinus spp. and Linognathus spp.; from the order of the Mallophaga, for example, Trichodectes spp. and Damalinea spp.; from the order of the Thysanoptera, for example *Hercinothrips femoralis* and *Thrips tabaci,* from the order of the Heteroptera, for example Eurygaster spp.; *Dysdercus intermedius, Piesma quadrata, Cimex lectularius, Rhodnius prolixus* and Triatoma spp.; from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp.; *Phorodon humuli, Rhopalosiphum padi,* Empoasca spp.; *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.; from the order of the Lepidoptera, for example *Pectinophora gossypiella, Bupalus piniarius, Chemimatobia brumate, Lithocolletis blancardella, Hyponomeuta padella, Plutella maculipennis, Malacosoma neustria, Euproctis chrysorrhoea,* Lymantria spp.; *Bucculatrix thurberiella, Phyllocnistis citrella,* Agrotis spp.; Euxoa spp.; Feltia spp.; *Earias insulana,* Heliothis spp.; *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.; from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.; from the class of the Arachnida, for example *Scorpio maurus* and *Latrodectus mactans;* from the order of the Acarina, for example *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., Bryobia praetiosa, Panonychus spp. and Tetranychus spp.

The plant-parasitic nematodes include Pratylenchus spp., *Radopholus similis, Ditylenchus dipsaci, Tylenchulus semi-penetrans,* Heterodera spp., Meloidogyne spp., Aphelenchoides spp., Longidorus spp., Xiphinema spp. and Trichodorus spp.

When used against pests harmful to health and pests of stored products, the active compounds are distinguished by an excellent residual activity on wood and clay as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose; aerosol propellants which are gaseous at normal temperature and pressures, such as halogenated hydrocarbons, e.g. dichlorodifluoromethane and trichlorofluoromethane, as well as butane, propane, nitrogen and carbon dioxide; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylene, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethylsulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose; emulsifying agents, such as nonionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl or polyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other arthropodicides, nematicides, and fungicides, or bactericides, rodenticides, herbicides, fertilizers, growth-regulating agents, bird repellents, plant nutrients, agents for improving soil structure, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0000001–100%, preferably 0.01–10%, by weight of the mixture. Thus, the present invention contemplates overall compositions which comprise mixtures of a conventional dispersible carrier vehicle such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0000001–100%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

When used against nematodes, the preparations are generally applied to an area of agriculture in amounts of 1 to 100 kg of active compound per hectare, and are then incorporated into the soil.

Furthermore, the present invention contemplates methods of selectively killing, combating or controlling pests, e.g. insects, acarids, nematodes and fungi, which comprises applying to at least one of correspondingly (a) such insects, (b) such acarids, (c) such nematodes, (d) such fungi, and (e) the corresponding habitat thereof, i.e. the locus to be protected, e.g. to a growing crop, to an area where a crop is to be grown or to a domestic animal, a corresponding combative or toxic amount, i.e. an insecticidally, acaricidally, nematicidally or fungicidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dry dressing, moist dressing, wet dressing, slurry dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

(a) The 3-tert.-butyl-5-hydroxy-pyrazoles (III) required as starting materials could be prepared, for example, as described below:

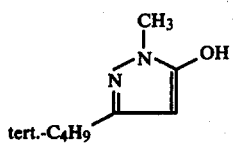

9.2 g (0.2 mol) of methylhydrazine were added dropwise to a mixture of 34.4 g (0.2 mol) of pivaloylacetic acid ethyl ester, 10.8 g (0.2 mol) of sodium methylate and 100 ml of methanol at 20° C. When the exothermic reaction had subsided, the reaction mixture was heated for 2 hours under reflux and then concentrated, the residue was taken up in 200 ml of water and this solution was acidified with concentrated hydrochloric acid to a pH of ca. 6. The resulting precipitate was filtered off, dried and recrystallized from isopropanol. 27 g (87% of theory) of 1-methyl-3-tert.-butyl-5-hydroxy-pyrazole were obtained in the form of colorless crystals of melting point 150° C.

The following compounds of the formula

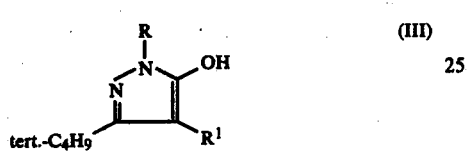

could be synthesized analogously:

Table 1

| R | $R^1$ | Yield (% of theory) | Melting point (°C.) |
|---|---|---|---|
| phenyl | H | 76 | 111 |
| phenyl | Cl | 48 | |
| 4-CF₃-phenyl | H | 28 | 81 |
| CH₃ | CH₃ | 35 | 152 |
| CH₃ | C₃H₇-iso | | |
| CH₃ | Br | | |

Table 1-continued

| R | $R^1$ | Yield (% of theory) | Melting point (°C.) |
|---|---|---|---|
| CH₃ | Cl | 49 | 140 |
| —CH₂—CH₂—C≡N | H | 61 | 107 |
| 3-Cl-phenyl | H | 36 | 56 |
| 4-CH₃-phenyl | H | 41 | 163 |
| H | H | 71 | 202 |

EXAMPLE 1

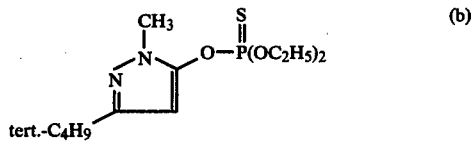

18.8 g (0.1 mol) of O,O-diethylthionophosphoric acid diester chloride were added dropwise to a mixture of 15.4 g (0.1 mol) of 1-methyl-3-tert.-butyl-5-hydroxy-pyrazole, 200 ml of acetonitrile and 14.5 g (0.105 mol) of potassium carbonate. The mixture was stirred for a further 3 hours at 40° C. and was then cooled, and the reaction mixture was poured into 300 ml of toluene. The toluene solution was washed with saturated sodium bicarbonate solution and water, dried over sodium sulphate and evaporated. After distilling off the toluene, 24 g (78% of theory) of O,O-diethyl-O-[1-methyl-3-tert.-butyl-pyrazol(5)yl]-thionophosphoric acid ester were obtained in the form of a yellow oil having a refractive index $n_D^{23}$ of 1.4832.

The following compounds of the formula

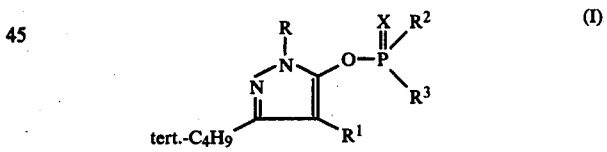

could be prepared analogously:

Table 2

| Compound No. | R | $R^1$ | $R^2$ | $R^3$ | X | Yield (% of theory) | Refractive index: |
|---|---|---|---|---|---|---|---|
| 2 | phenyl | H | OC₂H₅ | OC₂H₅ | S | 87 | $n_D^{23}$:1.5298 |
| 3 | phenyl | H | C₂H₅ | OC₂H₅ | S | 82 | $n_D^{21}$:1.5429 |
| 4 | phenyl | H | CH₃ | OC₂H₅ | S | 74 | $n_D^{21}$:1.5458 |

Table 2-continued

| Compound No. | R | R¹ | R² | R³ | X | Yield (% of theory) | Refractive index: |
|---|---|---|---|---|---|---|---|
| 5 | 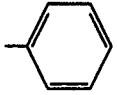 | H | CH₃ | OC₃H₇-iso | S | 74 | $n_D^{21}$:1.5438 |
| 6 | 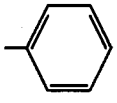 | H | OC₂H₅ | OC₂H₅ | O | 74 | $n_D^{21}$:1.5105 |
| 7 | 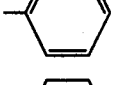 | H | OCH₃ | OCH₃ | S | 67 | $n_D^{21}$:1.5433 |
| 8 |  | H | 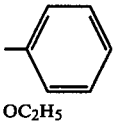 | OC₂H₅ | S | 50 | $n_D^{21}$:1.5746 |
| 9 |  | H | OC₂H₅ | NH—C₃H₇-iso | S | 63 | $n_D^{21}$:1.5442 |
| 10 | 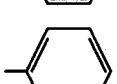 | Cl | OC₂H₅ | OC₂H₅ | S | 60 | $n_D^{21}$:1.5395 |
| 11 | 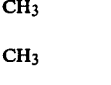 | Cl | OC₂H₅ | SC₃H₇-n | S | 56 | $n_D^{21}$:1.5600 |
| 12 | CH₃ | H | CH₃ | OC₃H₇-iso | S | 65 | $n_D^{21}$:1.4940 |
| 13 | CH₃ | H | OC₂H₅ | OC₂H₅ | O | 62 | $n_D^{21}$:1.4590 |
| 14 | CH₃ | H | OCH₃ | OCH₃ | S | 47 | $n_D^{21}$:1.4957 |
| 15 | CH₃ | H | CH₃ | OC₂H₅ | S | 51 | $n_D^{22}$:1.5016 |
| 16 | CH₃ | H | C₂H₅ | OC₂H₅ | S | 62 | $n_D^{22}$:1.4980 |
| 17 | CH₃ | H |  | OC₂H₅ | S | 52 | $n_D^{22}$:1.5462 |
| 18 | CH₃ | H | OC₂H₅ | NH—C₃H₇-iso | S | 68 | $n_D^{22}$:1.5068 |
| 19 | 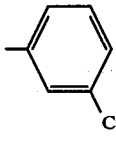 | H | OC₂H₅ | OC₂H₅ | S | 78 | $n_D^{23}$:1.4964 |
| 20 | 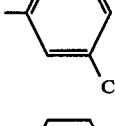 | H | OC₂H₅ | SC₃H₇-n | S | 77 | $n_D^{23}$:1.5148 |
| 21 | 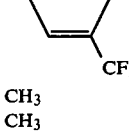 | H | C₂H₅ | OC₂H₅ | S | 77 | $n_D^{23}$:1.5027 |
| 22 | CH₃ | CH₃ | OCH₃ | OCH₃ | S | | |
| 23 | CH₃ | CH₃ | OC₂H₅ | OC₂H₅ | S | | |

Table 2-continued

| Compound No. | R | $R^1$ | $R^2$ | $R^3$ | X | Yield (% of theory) | Refractive index: |
|---|---|---|---|---|---|---|---|
| 24 | $CH_3$ | $CH_3$ | 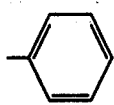 | $OC_2H_5$ | S | | |
| 25 | $CH_3$ | $CH_3$ | $CH_3$ | $OC_2H_5$ | S | | |
| 26 | $CH_3$ | $CH_3$ | $OC_2H_5$ | $SC_3H_7$-n | S | | |
| 27 | $CH_3$ | $C_3H_7$-iso | $OCH_3$ | $OCH_3$ | S | | |
| 28 | $CH_3$ | $C_3H_7$-iso | $OC_2H_5$ | $OC_2H_5$ | S | | |
| 29 | $CH_3$ | Br | $OCH_3$ | $OCH_3$ | S | | |
| 30 | $CH_3$ | Br | $OC_2H_5$ | $OC_2H_5$ | S | | |
| 31 | $CH_3$ | Br | 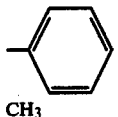 | $OC_2H_5$ | S | | |
| 32 | $CH_3$ | Br | $CH_3$ | $OC_2H_5$ | | | |
| 33 | $CH_3$ | Br | $OC_2H_5$ | $SC_3H_7$-n | S | | |
| 34 | $CH_3$ | H | $CH_3$ | $SC_4H_9$-sec. | S | 95 | $n_D^{23}$:1.5231 |
| 35 | $CH_3$ | H | $CH_3$ | $SC_3H_7$-n | S | 95 | $n_D^{23}$:1.5326 |
| 36 | $CH_3$ | H | $C_2H_5$ | $SC_4H_9$-sec. | S | 82 | $n_D^{23}$:1.5221 |
| 37 | $CH_3$ | Cl | $C_2H_5$ | $SC_4H_9$-sec. | S | 61 | $n_D^{23}$:1.5085 |
| 38 | $CH_3$ | Cl | $OC_2H_5$ | $OC_2H_5$ | S | 99 | $n_D^{27}$:1.4892 |
| 39 | $CH_3$ | Cl | $OCH_3$ | $OCH_3$ | S | 72 | $n_D^{23}$:1.5098 |
| 40 | $CH_3$ | Cl | $C_2H_5$ | $OC_2H_5$ | S | 93 | $n_D^{23}$:1.4905 |
| 41 | $CH_3$ | Cl | $OC_2H_5$ | $SC_3H_7$-n | S | 94 | $n_D^{23}$:1.5207 |
| 42 | $CH_3$ | Cl |  | $OC_2H_5$ | S | 95 | $n_D^{23}$:1.5419 |
| 43 | $CH_3$ | Cl | $OCH_2H_5$ | $OC_2H_5$ | O | 94 | $n_D^{23}$:1.4730 |
| 44 | $CH_3$ | Cl | $CH_3$ | $OC_2H_5$ | S | 89 | $n_D^{23}$:1.5168 |
| 45 | $(CH_2)_2CN$ | H | $OCH_3$ | $OCH_3$ | S | 76 | $n_D^{22}$:1.4930 |
| 46 | $(CH_2)_2CN$ | H | $OC_2H_5$ | $OC_2H_5$ | S | 91 | $n_D^{22}$:1.4908 |
| 47 | $(CH_2)_2CN$ | H | $C_2H_5$ | $OC_2H_5$ | S | 92 | $n_D^{22}$:1.5032 |
| 48 | $(CH_2)_2CN$ | H | $OC_2H_5$ | $SC_3H_7$-n | S | 93 | $n_D^{22}$:1.5177 |
| 49 | $(CH_2)_2CN$ | H | $OC_2H_5$ | $OC_2H_5$ | O | 91 | $n_D^{22}$:1.4669 |
| 50 | $(CH_2)_2CN$ | H | $CH_3$ | $OC_3H_7$-iso | S | 84 | $n_D^{22}$:1.5018 |
| 51 | $(CH_2)_2CN$ | H | $CH_3$ | $SC_4H_9$-sec. | S | 82 | $n_D^{22}$:1.5292 |
| 52 | $(CH_2)_2CN$ | H | 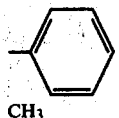 | $OC_2H_5$ | S | 92 | $n_D^{22}$:1.5393 |
| 53 | $(CH_2)_2CN$ | H | $CH_3$ | $OC_2H_5$ | S | 71 | $n_D^{22}$:1.5051 |
| 54 | $(CH_2)_2CN$ | H | $C_2H_5$ | $OCH_3$ | S | 86 | $n_D^{22}$:1.5050 |
| 55 | $(CH_2)_2CN$ | H | $OC_2H_5$ | $OC_3H_7$-n | S | 81 | $n_D^{22}$:1.4892 |
| 56 | $(CH_2)_2CN$ | H | $C_4H_9$-sec. | $OC_2H_5$ | S | 84 | $n_D^{22}$:1.4990 |
| 57 | 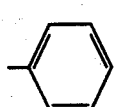 | H | $C_2H_5$ | $OC_2H_5$ | S | 69 | $n_D^{23}$:1.5440 |
| 58 | $C_3H_7$-iso | H | $OC_2H_5$ | $OC_2H_5$ | S | 65 | $n_D^{23}$:1.4740 |

Table 2-continued

| Compound No. | R | R¹ | R² | R³ | X | Yield (% of theory) | Refractive index |
|---|---|---|---|---|---|---|---|
| 59 | 4-CH₃-C₆H₄- | H | OC₂H₅ | OC₂H₅ | S | 89 | $n_D^{23}$:1.5290 |
| 60 | 4-CH₃-C₆H₄- | H | OC₂H₅ | OC₃H₇-n | S | 81 | $n_D^{23}$:1.5260 |
| 61 | 4-CH₃-C₆H₄- | H | OC₂H₅ | NH—C₃H₇-iso | O | 74 | $n_D^{23}$:1.5060 |
| 62 | 4-CH₃-C₆H₄- | H | OC₂H₅ | SC₃H₇-n | S | 75 | $n_D^{23}$:1.5490 |
| 63 | 4-CH₃-C₆H₄- | H | OC₂H₅ | NH—C₃H₇-iso | S | 68 | $n_D^{23}$:1.5390 |
| 64 | 4-CH₃-C₆H₄- | H | C₂H₅ | OC₂H₅ | S | 81 | $n_D^{23}$:1.5400 |
| 65 | 4-CH₃-C₆H₄- | H | C₂H₅ | OC₃H₇-n | S | 89 | $n_D^{23}$:1.5370 |
| 66 | H | H | OCH₃ | OCH₃ | S | 75 | $n_D^{25}$:1.5283 |
| 67 | H | H | C₂H₅ | OC₂H₅ | S | 98 | $n_D^{27}$:1.5083 |
| 68 | H | H | OC₂H₅ | OC₃H₇-n | S | 64 | $n_D^{27}$:1.4938 |
| 69 | CH₃ | H | CH₃ | OCH₃ | S | 88 | $n_D^{20}$:1,5063 |
| 70 | CH₃ | H | OC₂H₅ | SC₃H₇-n | O | 72 | $n_D^{20}$:1,4924 |

The insecticidal, acaricidal and nematicidal activity of the compounds of this invention is illustrated by the following biotest examples wherein the compounds of the present invention are each identified by the number (given in brackets) from the preparative examples and the known comparison compound is identified as follows:

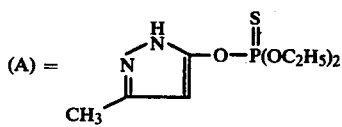

(A) =

EXAMPLE 2

Test insects *Blatta orientalis*
Solvent: Acetone

The active compound was taken up in the solvent at a rate of 2 g per liter. The solution so obtained was diluted with further solvent to the desired concentrations.

2.5 ml of the solution of the active compound were pipetted into a Petri dish. On the bottom of the Petri dish there was a filter paper with a diameter of about 9.5 cm. The Petri dish remained uncovered until the solvent had completely evaporated. The amount of active compound per square metre of filter paper varied with the concentration of the solution of active compound. About 10 test insects were then placed in the Petri dish and it was covered with a glass lid.

The condition of the test insects was observed 3 days after the commencement of the experiments. The destruction, in %, was determined. 100% denoted that all of the test insects had been killed; 0% denoted that none of the test insects had been killed.

The active compounds, the concentrations of the active compounds, and the results can be seen from the following table:

Table 3

| Active compound | Active compound concentration of the solution in % | Degree of destruction in % |
|---|---|---|
| (A) | 0.02 | 0 |
| (14) | 0.02 | 100 |
| (1) | 0.02 | 100 |
| (15) | 0.02 | 100 |
| (16) | 0.02 | 100 |
| (12) | 0.02 | 100 |

(*Blatta orientalis*)

EXAMPLE 3

LT$_{100}$ test for Diptera
Test insects: *Aëdes aegypti*
Solvent: Acetone

The active compound was dissolved in the solvent at a rate of 2 g per liter. The solution so obtained was diluted with further solvent to the desired lower concentrations.

2.5 ml of the solution of active compound were pipetted into a Petri dish. On the bottom of the Petri dish there was a filter paper with a diameter of about 9.5 cm. The Petri dish remained uncovered until the solvent had completely evaporated. The amount of active compound per square meter of filter paper varied with the concentration of the solution of active compound. About 25 test insects were then placed in the Petri dish and it was covered with a glass lid.

The condition of the test insects was continuously observed. The time which was necessary for 100% destruction was determined.

The active compounds, the concentrations of the active compounds and the times at which there was 100% destruction can be seen from the following table:

Table 4

(LT$_{100}$ test for *Diptera/Aëdes aegypti*)

| Active compound | Active compound concentration of the solution in % | LT$_{100}$ in minutes |
|---|---|---|
| (A) | 0.2 | 180 |
| (14) | 0.02 | 60 |
| (1) | 0.02 | 60 |
| (15) | 0.02 | 60 |
| (16) | 0.02 | 60 |
| (12) | 0.02 | 60 |
| (17) | 0.2 | 120 |
| (18) | 0.2 | 120 |
| (45) | 0.2 | 120 |
| (46) | 0.2 | 120 |
| (47) | 0.2 | 180 |
| (49) | 0.2 | 60 |
| (53) | 0.2 | 60 |
| (54) | 0.2 | 120 |
| (57) | 0.2 | 120 |
| (21) | 0.2 | 60 |
| (10) | 0.2 | 60 |
| (13) | 0.2 | 60 |

EXAMPLE 4

Myzus test (contact action)
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*) which had been heavily infested with peach aphids (*Myzus persicae*) were sprayed with the preparation of the active compound until dripping wet.

After the specified periods of time, the degree of destruction was determined as a percentage: 100% meant that all of the aphids were killed whereas 0% meant that none of the aphids were killed.

The active compounds, the concentrations of the active compounds, the evaluation times and the results can be seen from the following table:

Table 5

(*Myzus* test)

| Active compound | Active compound concentration in % | Degree of destruction in % after 1 day |
|---|---|---|
| (A) | 0.1 | 99 |
| | 0.01 | 40 |
| | 0.001 | 0 |
| (14) | 0.1 | 100 |
| | 0.01 | 100 |
| | 0.001 | 40 |
| (1) | 0.1 | 100 |
| | 0.01 | 100 |
| | 0.001 | 85 |
| (13) | 0.1 | 100 |
| | 0.01 | 100 |
| | 0.001 | 75 |
| (46) | 0.1 | 100 |
| | 0.01 | 100 |
| | 0.001 | 70 |
| (54) | 0.1 | 100 |
| | 0.01 | 100 |
| | 0.001 | 99 |
| (15) | 0.1 | 100 |
| | 0.01 | 100 |
| | 0.001 | 100 |
| (53) | 0.1 | 100 |
| | 0.01 | 100 |
| | 0.001 | 99 |
| (47) | 0.1 | 100 |
| | 0.01 | 100 |
| | 0.001 | 70 |
| (16) | 0.1 | 100 |
| | 0.01 | 100 |
| | 0.001 | 100 |
| (12) | 0.1 | 100 |
| | 0.01 | 100 |
| | 0.001 | 100 |
| (50) | 0.1 | 100 |
| | 0.01 | 100 |
| | 0.001 | 95 |
| (48) | 0.1 | 100 |
| | 0.01 | 100 |
| | 0.001 | 99 |
| (34) | 0.1 | 100 |
| | 0.01 | 100 |
| | 0.001 | 100 |
| (51) | 0.1 | 100 |
| | 0.01 | 100 |
| | 0.001 | 100 |
| (18) | 0.1 | 100 |
| | 0.01 | 100 |
| | 0.001 | 99 |
| (17) | 0.1 | 100 |
| | 0.01 | 100 |
| | 0.001 | 100 |

EXAMPLE 5

Tetranychus test (resistant)
Solvent: 3 parts by weight of acetone
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Bean plants (*Phaseolus vulgaris*) which were heavily infested with the two-spotted spider mite (*Tetranychus*

*urticae*) in all stages of development were sprayed with the preparation of the active compound until dripping wet.

After the specified periods of time, the degree of destruction was determined as a percentage: 100% meant that all of the spider mites were killed whereas 0% meant that none of the spider mites were killed.

The active compounds, the concentrations of the active compounds, the evaluation times and the results can be seen from the following table:

Table 6

(*Tetranychus* test, resistant)

| Active compound | Active compound concentration in % | Degree of destruction in % after 2 days |
|---|---|---|
| (A) | 0.1 | 50 |
|  | 0.01 | 0 |
| (48) | 0.1 | 100 |
|  | 0.01 | 95 |
| (34) | 0.1 | 100 |
|  | 0.01 | 20 |
| (51) | 0.1 | 100 |
|  | 0.01 | 99 |

EXAMPLE 6

Test insect: *Phorbia antiqua* grubs in the soil
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was practically immaterial, the only decisive factor being the amount by weight of active compound per unit volume of soil, which is quoted hereinafter in ppm (=mg/l). The treated soil was filled into pots and the pots were left to stand at room temperature.

After 24 hours the test insects were introduced into the treated soil and after a further 2 to 7 days the degree of effectiveness of the active compound was determined in % by counting the dead and the live test insects. The degree of effectiveness was 100% if all of the test insects had been killed and was 0% if exactly as many test insects were still alive as in the case of the untreated control.

The active compounds, the amounts used and the results can be seen from the table which follows:

Table 7

(*Phorbia antiqua* grubs in the soil)

| Active compound | Degree of destruction in % at an active compound concentration of 5 ppm |
|---|---|
| (A) | 0 |
| (58) | 100 |
| (2) | 100 |
| (1) | 100 |
| (3) | 100 |
| (7) | 100 |
| (12) | 100 |
| (17) | 100 |

Table 7-continued (*Phorbia antiqua* grubs in the soil)

| Active compound | Degree of destruction in % at an active compound concentration of 5 ppm |
|---|---|
| (47) | 100 |
| (50) | 100 |

EXAMPLE 7

Test insect: *Tenebrio molitor* larvae in the soil
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was practically immaterial, the only decisive factor being the amount by weight of active compound per unit volume of soil, which is quoted hereinafter in ppm (=mg/l). The treated soil was filled into pots and the pots were left to stand at room temperature.

After 24 hours the test insects were introduced into the treated soil and after a further 2 to 7 days the degree of effectiveness of the active compound was determined in % by counting the dead and live test insects. The degree of effectiveness was 100% if all of the test insects had been killed and was 0% if exactly as many test insects were still alive as in the case of the untreated control.

The active compounds, the amounts used and the results can be seen from the table which follows:

Table 8

(Critical concentration test/soil insects)
(*Tenebrio molitor* larvae in the soil)

| Active compound | Degree of destruction in % at an active compound concentration of 5 ppm |
|---|---|
| (A) | 0 |
| (19) | 100 |
| (1) | 100 |
| (12) | 100 |
| (17) | 100 |

EXAMPLE 8

Test nematode: *Meloidogyne incognita*
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil which was heavily infested with the test nematodes. The concentration of the active compound in the preparation was of practically no importance; only the amount of active compound per unit volume of soil, which is given hereinafter in ppm (=mg/l), was decisive. The treated soil was filled into pots, lettuce was sown in and the pots were kept at a greenhouse temperature of 27° C.

After 4 weeks, the lettuce roots were examined for infestation with nematodes (root galls), and the degree of effectiveness of the active compound was determined as a percentage. The degree of effectiveness was 100% when infestation was completely avoided; it was 0% when the infestation was exactly the same as in the case of the control plants in untreated soil which had been infested in the same manner.

The active compound, the amounts applied and the results can be seen from the following table:

Table 9

| (Meloidogyne incognita) | |
| --- | --- |
| Active compound | Degree of destruction in % at an active compound concentration of 5ppm |
| (A) | 0 |
| (67) | 100 |
| (12) | 100 |
| (16) | 100 |
| (18) | 100 |

It will be appreciated that the instant specification and examples are set forth by way of illustration and not limitation, and that various modifications and changes may be made without departing from the spirit and scope of the present invention.

What is claimed is:

1. A compound of the formula

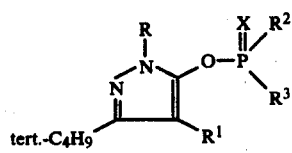

in which
R is hydrogen, alkyl with 1 to 4 carbon atoms, cyanoalkyl with 1 to 4 alkyl carbon atoms, or phenyl optionally carrying at least one halogen, or halogenoalkyl, alkyl or alkylthio substituent wherein the alkyl has up to 4 carbon atoms,
$R^1$ is hydrogen, halogen, or alkyl or alkylthio with 1 to 6 carbon atoms.
$R^2$ is alkoxy or alkyl with 1 to 8 carbon atoms, or phenyl,
$R^3$ is alkoxy with 1 to 6 carbon atoms, and
X is oxygen or sulphur.

2. A compound according to claim 1, in which
R is hydrogen, alkyl or cyanoalkyl with 1 to 4 alkyl carbon atoms, phenyl, or phenyl carrying at least one chlorine, methyl, ethyl or trifluoromethyl substituent,
$R^1$ is hydrogen, chlorine, bromine or alkyl with 1 to 6 carbon atoms, and
X is sulphur.

3. A compound according to claim 1 wherein such compound is
O,O-diethyl-O-[1-methyl-3-tert.-butyl-pyrazol(5)yl]-thionophosphoric acid ester of the formula

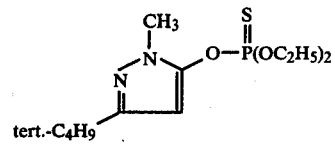

4. A compound according to claim 1 wherein such compound is
O,O-dimethyl-O-[1-methyl-3-tert.-butyl-pyrazol(-5)yl]-thionophosphoric acid ester of the formula

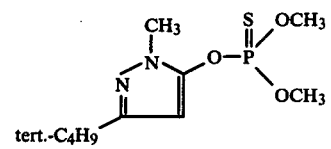

5. A compound according to claim 1 wherein such compound is
O-ethyl-O-[1-methyl-3-tert.-butyl-pyrazol(5)yl-]-methanethionophosphonic acid ester of the formula

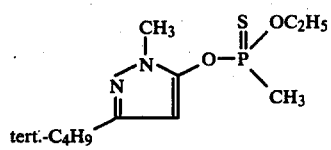

6. A compound according to claim 1 wherein such compound is
O-ethyl-O-[1-methyl-3-tert.-butyl-pyrazol(5)yl]-ethanethionophosphonic acid ester of the formula

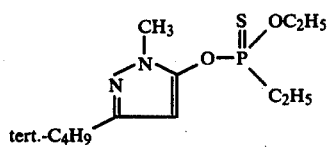

7. A compound according to claim 1 wherein such compound is
O-methyl-O-[1-(2-cyanoethyl)-3-tert.-butyl-pyrazol(-5)yl]ethanethionophosphonic acid ester of the formula

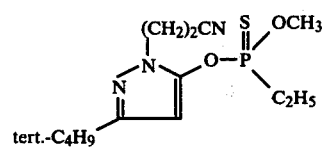

8. An arthropodicidal, nematicidal or fungicidal composition of matter comprising an arthropodicidally, nematicidally or fungicidally effective amount of a compound according to claim 1 in admixture with a diluent.

9. A method of combating arthropods, nematodes or fungi which comprises applying to such arthropods, nematodes or fungi or to a habitat thereof an arthropodicidally, nematicidally or fungicidally effective amount of a compound according to claim 1.

10. The method according to claim 9, wherein such compound is

O,O-diethyl-O-[1-methyl-3-tert.-butyl-pyrazol(-5)yl]thiono-phosphoric acid ester, O,O-dimethyl-O-[1-methyl-3-tert.-butyl-pyrazol(-5)yl]thiono-phosphoric acid ester, O-ethyl-O-[1-methyl-3-tert.-butyl-pyrazol(5)yl]methanethiono-phosphonic acid ester, O-ethyl-O-[1-methyl-3-tert.-butyl-pyrazol(5)yl]ethanethiono-phosphonic acid ester, or O-methyl-O-[1-(2-cyanoethyl)-3-tert.-butyl-pyrazol(5) yl]-ethanethionophosphonic acid ester.

* * * * *